US008366998B2

(12) United States Patent
Wakamiya et al.

(10) Patent No.: US 8,366,998 B2
(45) Date of Patent: Feb. 5, 2013

(54) SAMPLE ANALYZER AND SAMPLE ANALYZING METHOD

(75) Inventors: Yuji Wakamiya, Hyogo (JP); Tomohiro Okuzaki, Hyogo (JP); Hisato Takehara, Hyogo (JP)

(73) Assignee: Sysmex Corporation (JP)

( * ) Notice: Subject to any disclaimer, the term of this patent is extended or adjusted under 35 U.S.C. 154(b) by 811 days.

(21) Appl. No.: 12/284,271

(22) Filed: Sep. 19, 2008

(65) Prior Publication Data

US 2009/0215184 A1    Aug. 27, 2009

(30) Foreign Application Priority Data

Sep. 20, 2007   (JP) .................................. 2007-243692

(51) Int. Cl.
*G01N 21/00* (2006.01)
*G01N 35/00* (2006.01)

(52) U.S. Cl. ............ 422/67; 422/68.1; 422/105; 436/43; 436/50; 436/55; 700/266

(58) Field of Classification Search .................... 436/50, 436/55, 43; 422/105, 50, 402, 62, 68.1, 67; 700/266, 296
See application file for complete search history.

(56) References Cited

U.S. PATENT DOCUMENTS

| 693,764 | A | * | 2/1902 | Washburn | 24/706.6 |
|---|---|---|---|---|---|
| 3,767,364 | A | * | 10/1973 | Ritchie et al. | 422/50 |
| 3,883,305 | A | * | 5/1975 | Hoskins et al. | 422/65 |
| 3,960,497 | A | * | 6/1976 | Acord | 422/67 |
| 4,236,894 | A | * | 12/1980 | Sommervold | 436/43 |
| 5,316,727 | A | * | 5/1994 | Suzuki et al. | 422/68.1 |
| 5,428,470 | A | * | 6/1995 | Labriola, II | 398/109 |
| 5,576,215 | A | * | 11/1996 | Burns et al. | 436/50 |
| 5,695,718 | A | * | 12/1997 | Imai et al. | 422/62 |
| 5,728,351 | A | * | 3/1998 | Carver, Jr. | 422/73 |
| 5,827,478 | A | * | 10/1998 | Carey et al. | 422/64 |
| 6,498,037 | B1 | * | 12/2002 | Carey et al. | 436/50 |
| 6,740,296 | B1 | * | 5/2004 | Inoue | 422/106 |
| 6,787,112 | B1 | * | 9/2004 | Turner et al. | 422/130 |
| 6,812,032 | B1 | * | 11/2004 | Carver et al. | 436/63 |
| 6,979,569 | B1 | * | 12/2005 | Carver et al. | 436/63 |
| 7,029,922 | B2 | * | 4/2006 | Miller | 436/180 |
| 7,067,319 | B2 | * | 6/2006 | Wills et al. | 436/37 |
| 7,618,587 | B2 | * | 11/2009 | Kawate | 422/73 |
| 7,754,149 | B2 | * | 7/2010 | Sugiyama | 422/67 |
| 7,763,468 | B2 | * | 7/2010 | Kawai | 436/55 |
| 7,972,559 | B2 | * | 7/2011 | Goix et al. | 422/73 |
| 8,017,080 | B2 | * | 9/2011 | Sasanuma et al. | 422/82.12 |

(Continued)

FOREIGN PATENT DOCUMENTS

JP     2003-279583    10/2003

*Primary Examiner* — Brian R Gordon
(74) *Attorney, Agent, or Firm* — Brinks Hofer Gilson & Lione

(57) ABSTRACT

A sample analyzer includes an order receiver for receiving an analyzing order of a sample having analyzing item information; an analyzing section for analyzing a sample according to the analyzing order received by the order receiver; a calculator for counting a first number of analyses by the analyzing section in a first counting period, and a second number of analyses by the analyzing section in a second counting period different from the first counting period; a selection receiver for receiving a selection of either one of the first counting period and the second counting period; an output section; and an output controller for outputting a number of analyses in the counting period received by the selection receiver to the output section based on the counted result by the calculator is disclosed. A sample analyzing method is also disclosed.

13 Claims, 9 Drawing Sheets

U.S. PATENT DOCUMENTS

| | | | |
|---|---|---|---|
| 8,043,560 B2* | 10/2011 | Okumoto et al. | 422/64 |
| 2003/0054557 A1* | 3/2003 | Devlin, Sr. | 436/50 |
| 2003/0157721 A1* | 8/2003 | Turner et al. | 436/34 |
| 2004/0087031 A1* | 5/2004 | Simon, Jr. | 436/100 |
| 2005/0220671 A1* | 10/2005 | Stein et al. | 422/67 |
| 2007/0172390 A1 | 7/2007 | Ootani et al. | |
| 2007/0175284 A1* | 8/2007 | Oonuma et al. | 73/864.21 |
| 2008/0145275 A1* | 6/2008 | Chen | 422/68.1 |
| 2008/0281471 A1* | 11/2008 | Smith et al. | 700/266 |

\* cited by examiner

FIG. 8

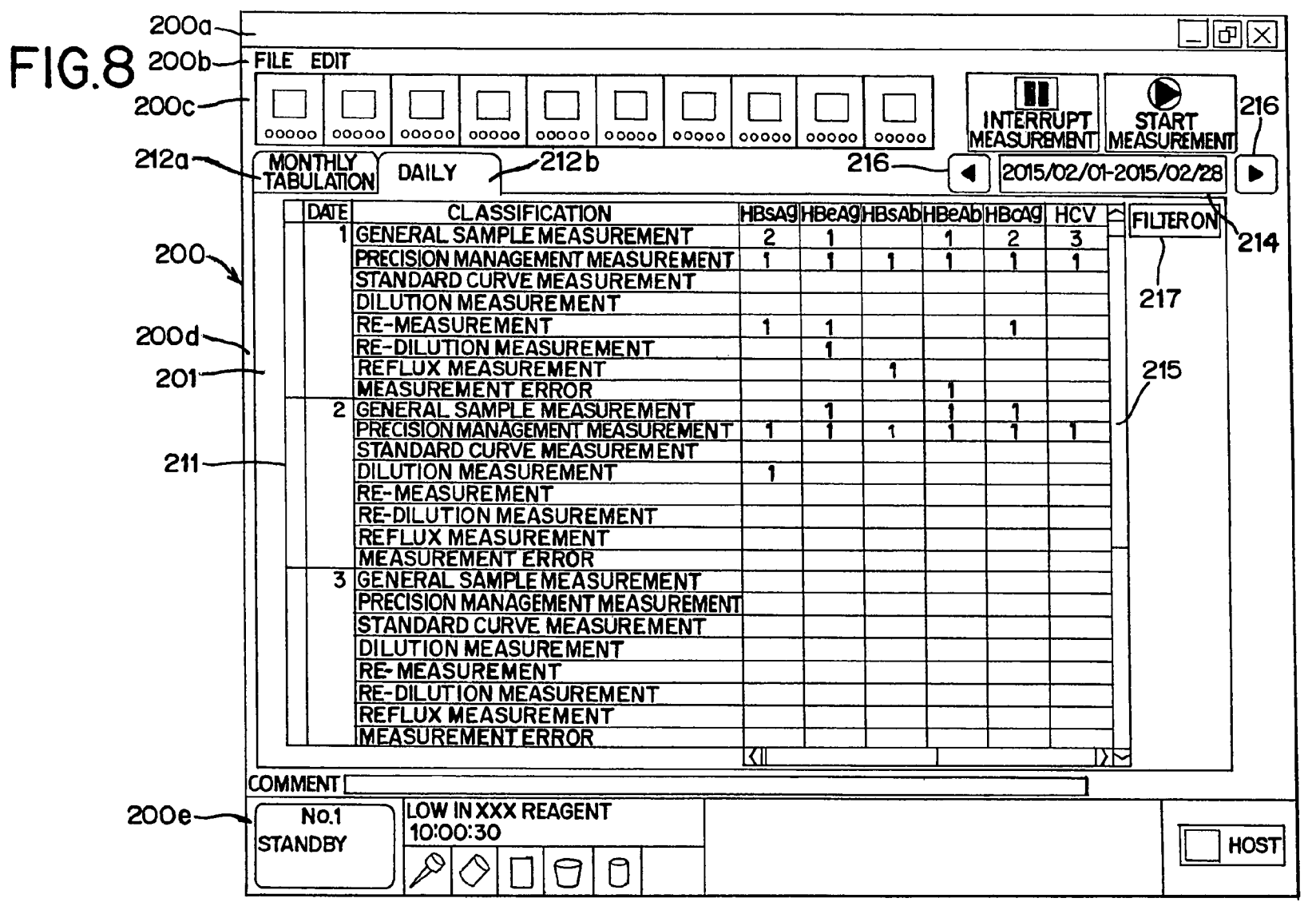

| DATE | CLASSIFICATION | HBsAg | HBeAg | HBsAb | HBeAb | HBcAb | HCV |
|---|---|---|---|---|---|---|---|
| 1 | GENERAL SAMPLE MEASUREMENT | 2 | 1 | | | 2 | 3 |
| | PRECISION MANAGEMENT MEASUREMENT | 1 | 1 | 1 | 1 | 1 | 1 |
| | STANDARD CURVE MEASUREMENT | | | | | | |
| | DILUTION MEASUREMENT | | | | | | |
| | RE-MEASUREMENT | | 1 | 1 | | | |
| | RE-DILUTION MEASUREMENT | | | | | | |
| | REFLUX MEASUREMENT | | | | | | |
| | MEASUREMENT ERROR | | | | | | |
| 2 | GENERAL SAMPLE MEASUREMENT | 1 | 1 | 1 | 1 | 2 | 1 |
| | PRECISION MANAGEMENT MEASUREMENT | | 1 | 1 | 1 | 1 | 1 |
| | STANDARD CURVE MEASUREMENT | | | | | | |
| | DILUTION MEASUREMENT | | | | | | |
| | RE-MEASUREMENT | | | | | | |
| | RE-DILUTION MEASUREMENT | | | | | | |
| | REFLUX MEASUREMENT | | | | | | |
| | MEASUREMENT ERROR | | | | | | |
| 3 | GENERAL SAMPLE MEASUREMENT | | | | | | |
| | PRECISION MANAGEMENT MEASUREMENT | | | | | | |
| | STANDARD CURVE MEASUREMENT | | | | | | |
| | DILUTION MEASUREMENT | | | | | | |
| | RE-MEASUREMENT | | | | | | |
| | RE-DILUTION MEASUREMENT | | | | | | |
| | REFLUX MEASUREMENT | | | | | | |
| | MEASUREMENT ERROR | | | | | | |

SAMPLE ANALYZER AND SAMPLE ANALYZING METHOD

RELATED APPLICATIONS

This application claims priority under 35 U.S.C. §119 to Japanese Patent Application No. JP2007-243692 filed Sep. 20, 2007, the entire content of which is hereby incorporated by reference.

FIELD OF THE INVENTION

The present invention relates to a sample analyzer, such as immune analyzer and blood coagulation analyzer, for analyzing samples and sample analyzing method.

BACKGROUND

In hospitals and inspection institutes, a sample analyzer for measuring items related to the aspects of the sample (specimen) such as blood is used. Various measurements such as general sample examination, re-examination, and reflux examination are performed on various measurement items such as HBsAg and HBeAg in the immune analyzer.

Since such sample analyzer is very expensive, great expense is required to introduce the sample analyzer. Thus, instead of having the user purchase the sample analyzer, it is contemplated that the sample analyzer is leased to the user with consumable goods and maintenance service, and the utility rate is set according to the usage frequency such as number of measurements (see e.g., Japanese Laid-Open Patent Publication JP2003-279583).

Japanese Laid-Open Patent Publication JP2003-279583 discloses a technique of connecting the analyzer to an information terminal by way of a network, sending the test number data by analyzing items to the information terminal via the network for every sample type such as precision management specimen measured in the analyzer, patient sample, reexamination sample and the like, accumulating the test number data for one month etc. on the information terminal side, calculating the utility rate of the user based on the totalized result of the test number data of the relevant period and the test unit price, and providing the information on the utility rate to the analyzer side via the network, thus using for collecting the rate.

Japanese Laid-Open Patent Publication JP2003-279583 discloses performing, in addition to cost management as described above, precision management of the analyzer, operation management, and inventory control of consumable goods through the network.

On the user side using the sample analyzer, there is a demand to uniquely recognize the short-term operation state such as one day or one week of the analyzer, or mid to long-term operation state such as one month, three months, or one year with various patterns, and using the same for various managements of the analyzer such as income and expenditure management of hospitals and utility management of consumable goods. However, in the technique of Japanese Laid-Open Patent Publication JP2003-279583, the number of tests is totalized, but the purpose of use is the calculation of the utility rate of the analyzer, and thus there is no need to totalize the number of tests other than in the counting period (e.g., one month) necessary for the calculation of the utility rate. Thus, the relevant totalized result is insufficient to be used for various managements described above.

BRIEF SUMMARY

The scope of the present invention is defined solely by the appended claims, and is not affected to any degree by the statements within this summary.

A first aspect of the present invention is a sample analyzer comprising: an order receiver for receiving an analyzing order of a sample having analyzing item information; an analyzing section for analyzing a sample according to the analyzing order received by the order receiver; a calculator for counting a first number of analyses by the analyzing section in a first counting period, and a second number of analyses by the analyzing section in a second counting period different from the first counting period; a selection receiver for receiving a selection of either one of the first counting period and the second counting period; an output section; and an output controller for outputting a number of analyses in the counting period received by the selection receiver to the output section based on the counted result by the calculator.

A second aspect of the present invention is a sample analyzer comprising: an order receiver for receiving an analyzing order of a sample having analyzing item information; an analyzing section for mixing a sample and a reagent according to the analyzing order received by the order receiver, and analyzing the sample; a designation receiver for receiving designation of an arbitrary counting period for counting a number of analyses; a calculator for counting the number of analyses by the analyzing section in the counting period received by the designation receiver; an output section; and an output controller for outputting the number of analyses by the analyzing section in the counting period to the output section.

A third aspect of the present invention is a sample analyzing method comprising the steps of: (a) receiving an analyzing order of a sample having analyzing item information; (b) mixing a sample and a reagent according to the received analyzing order, and analyzing the sample; (c) counting a first number of analyses in a first counting period, and a second number of analyses in a second counting period different from the first counting period; (d) receiving a selection of either one of the first counting period and the second counting period; and (e) outputting a number of analyses in the received counting period based on the counted by (C).

A fourth aspect of the present invention is a sample analyzing method comprising the steps of: (a) receiving an analyzing order of a sample having analyzing item information; (b) mixing a sample and a reagent according to the received analyzing order, and analyzing the sample; (c) receiving designation of an arbitrary counting period for counting a number of analyses; (d) counting a number of analyses in the designated counting period; and (e) outputting the number of analyses in the designated counting period.

BRIEF DESCRIPTION OF THE DRAWINGS

FIG. 8 is a view showing the measurement count history screen; and

DETAILED DESCRIPTION OF THE PREFERRED EMBODIMENTS

The preferred embodiments of the present invention will be described hereinafter with reference to the drawings.
[Overall Configuration of Apparatus]

Figure 1:
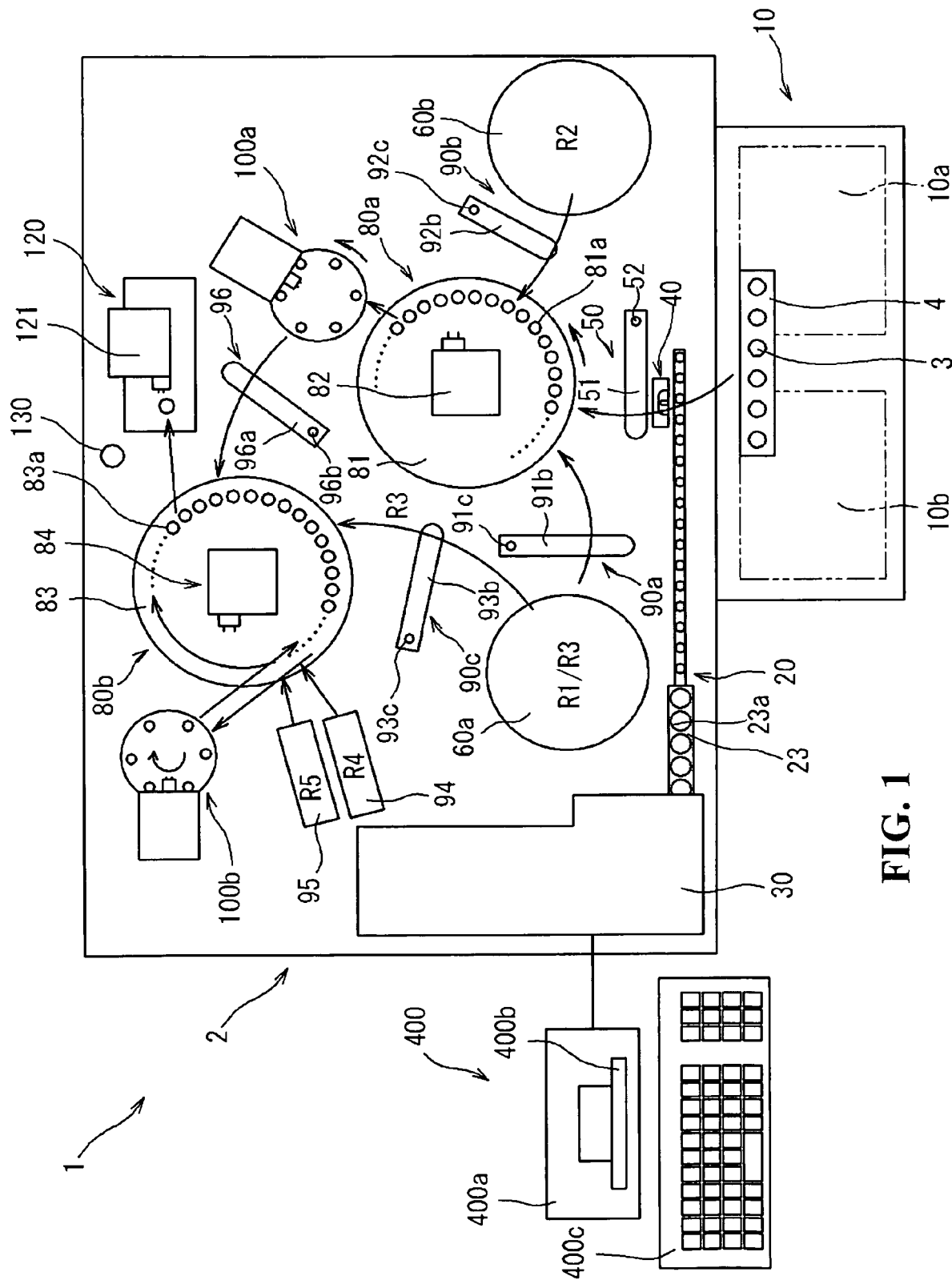
FIG. 1 is a plane explanatory view showing an overall configuration of one embodiment of an immune analyzer of the present invention.

FIG. 1 is a plane explanatory view showing an overall configuration of an immune analyzer (sample analyzer) according to one embodiment of the present invention.

An immune analyzer 1 according to one embodiment of the present invention is an apparatus for carrying out examinations on various measurement items (analyzing items) such as hepatitis B, hepatitis C, tumor marker, and thyroid hormone using sample (specimen) such as blood. As shown in frame format view in FIG. 1, the immune analyzer 1 is mainly configured by a measurement unit (analyzing section) 2 including a plurality of mechanisms (components), and a control device 400 (see FIG. 3) or a data processing unit electrically connected to the measurement unit 2.

Figure 2:
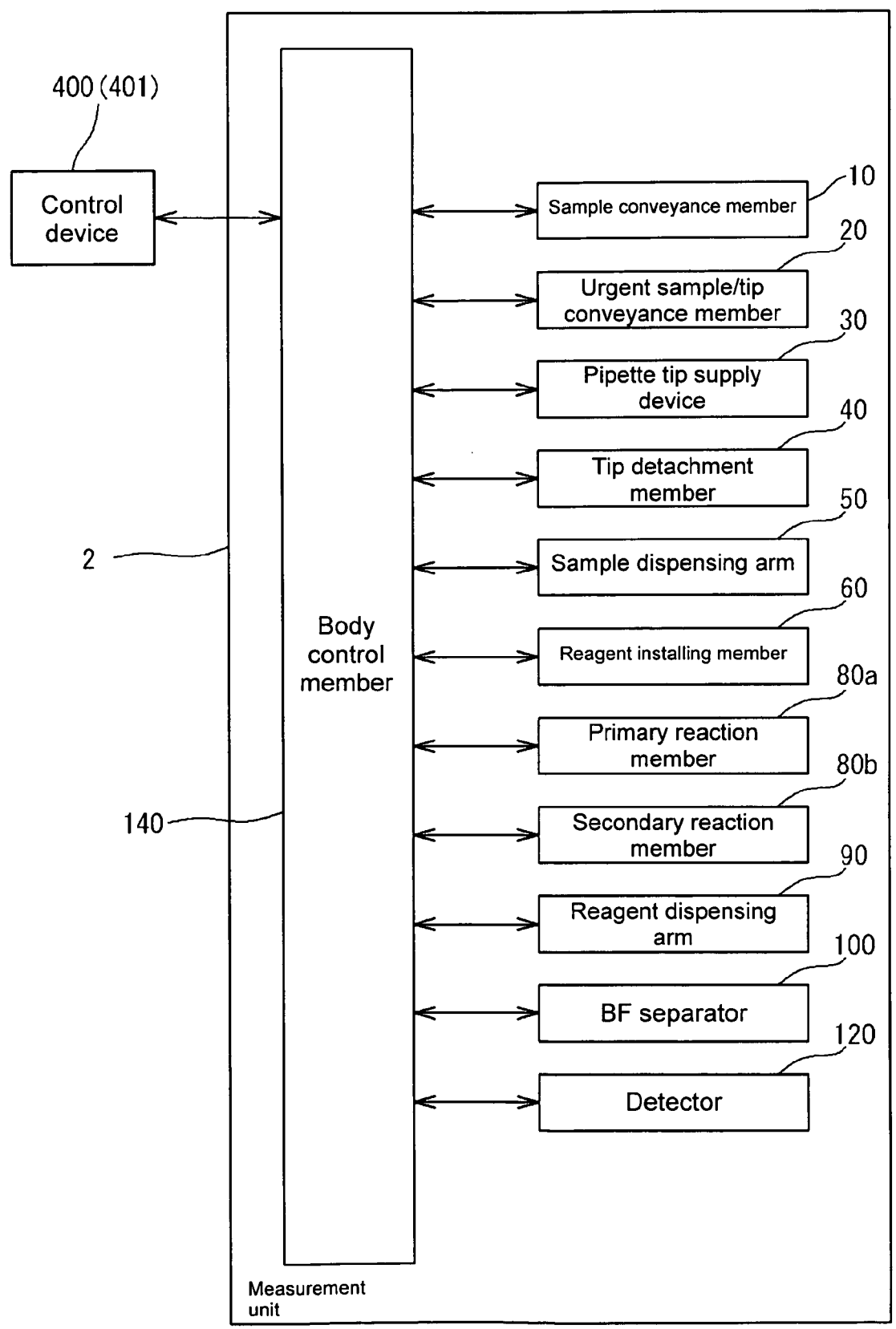
FIG. 2 is a block diagram showing a configuration of a measurement unit in the immune analyzer shown in FIG. 1.

The measurement unit 2 includes a sample conveyance member (sampler) 10, an urgent sample/tip conveyance member 20, a pipette tip supply device 30, a tip detachment member 40, a sample dispensing arm 50, reagent installing members 60a and 60b, a primary reaction member 80a and a secondary reaction member 80b, reagent dispensing arms 90a, 90b, and 90c, a primary BF separator 100a and a secondary BF separator 100b, a detector 120, and a body control member 140 (see FIG. 2) for performing operation control of mechanisms such as the sample conveyance member (sampler) 10 and the sample dispensing arm 50. In the immune analyzer 1 according to the present embodiment, the disposable pipette tip is changed every time when aspiration and discharge of specimen are performed in order to suppress the sample which aspirated and discharged by the sample dispensing arm 50 from mixing with other samples.

In the immune analyzer 1, after binding magnetic particles (R2 reagent) to a trapped antibody (R1 reagent) bound to an antigen contained in the sample such as blood to be measured, the bound antigen, the trapped antibody and the magnetic particles are attracted to a magnet of the primary BF (Bound Free) separator 100a to remove R1 reagent containing non-reactive (free) trapped body. A labeled antibody (R3 reagent) is bonded to the antigen bounded with the magnetic particles, and thereafter, the bound magnetic particles, the antigen, and the labeled antibody are attracted to a magnet of the secondary BF separator 100b to remove the R3 reagent containing non-reactive (free) labeled antibody. Furthermore, a luminescent substrate (R5 reagent) that emits light in the reaction process with the labeled antibody is added, and thereafter, a light emission amount generated through the reaction of the labeled antibody and the luminescent substrate is measured. Through such processes, the antigen contained in the sample that bonds with the labeled antibody is quantitatively measured.

[Configuration of Control Device]

The control device 400 is configured by a personal computer 401 (PC), and includes a control member 400a, a display member 400b, and an input member (input means) 400c such as a keyboard and a mouse, as shown in FIG. 1. The control member 400a has a function of performing operation control of each mechanism in the measurement unit 2, and analyzing optical information of the sample obtained in the measurement unit 2. The control member 400a consists of CPU, ROM, RAM, and the like. The display member 400b is used to display information such as analysis results obtained by the control member 400a, and to a measurement count history screen 201 etc. to be hereinafter described.

Figure 3:
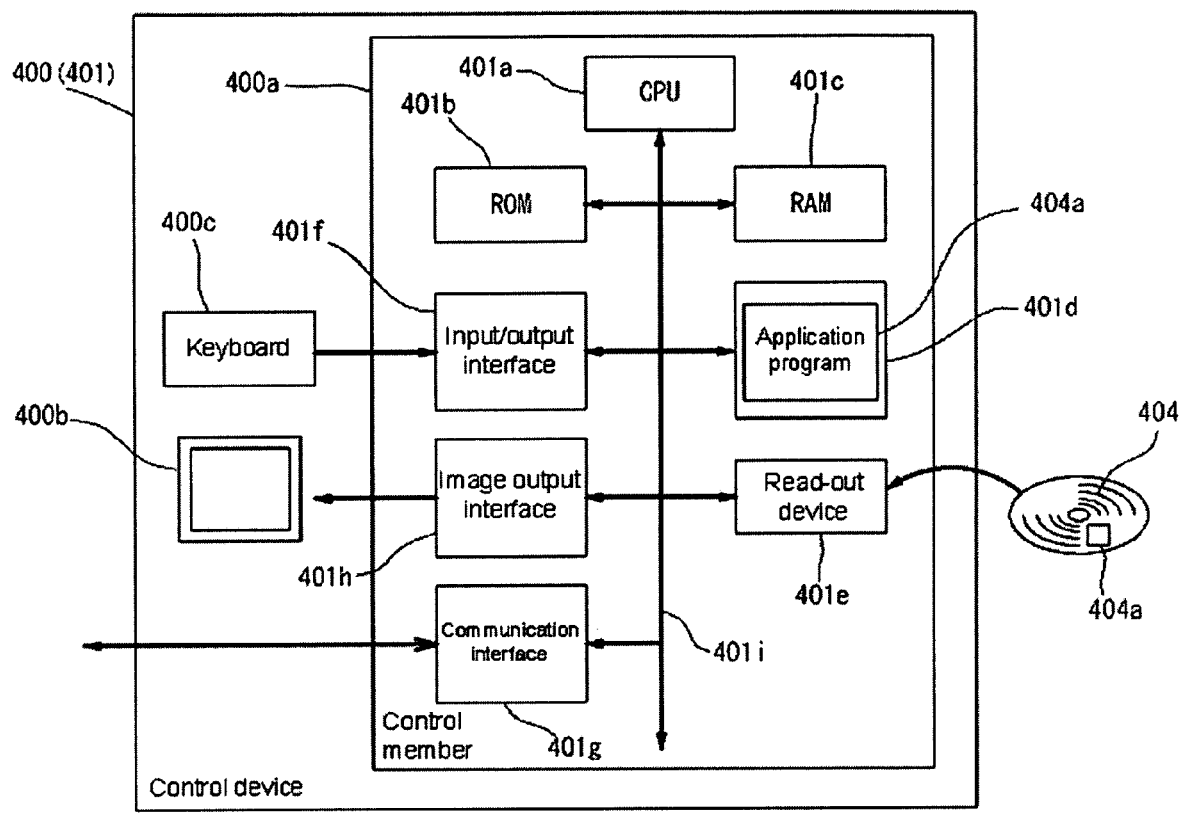
FIG. 3 is a block diagram of a control device in the immune analyzer shown in FIG. 1.

The configuration of the control device 400 will now be described. As shown in FIG. 3, the control member 400a is mainly configured by a storage member such as CPU 401a, ROM 401b, RAM 401c, and hard disc 401d, a read-out device 401e, an input/output interface 401f, a communication interface 401g, and an image output interface 401h.

The CPU 401a, the ROM 401b, the RAM 401c, the hard disc 401d, the read-out device 401e, the input/output interface 401f, the communication interface 401g, and the image output interface 401h are connected by a bus 401i.

The CPU 401a executes computer programs stored in the ROM 401b and the computer programs loaded in the RAM 401c. The computer 401 serves as the control device 400 when the CPU 401a executes the application program 404a, as hereinafter described.

The ROM 401b is configured by mask ROM, PROM, EPROM, EEPROM, and the like, and is recorded with computer programs to be executed by the CPU 401a, data used for the same, and the like.

The RAM 401c is configured by SRAM, DRAM, and the like. The RAM 401c is used to read out the computer programs recorded on the ROM 401b and the hard disc 401d. The RAM 401c is used as a work region of the CPU 401a when executing the computer programs.

The hard disc 401d is installed with various computer programs 404a to be executed by the CPU 401a such as operating system and application program, as well as data used in executing the computer program. The application program for registering measurement order and application program for totalizing the number of measurements to be hereinafter described and displaying the totalized result are also installed in the hard disc 401d.

The read-out device 401e is configured by flexible disc drive, CD-ROM drive, DVD-ROM drive, and the like, and is able to read out computer programs and data recorded on a portable recording medium 404. The application program 404a according to the present embodiment is stored in the portable recording medium 404, where the computer 401 reads out the application program 404a from the portable recording medium 404, and installs the application program 404a to the hard disc 401d.

The application program 404a is not only provided by the portable recording medium 404, but is also provided through communication line (wired or wireless) from external devices communicatably connected with the computer 401 through the communication line. For instance, the application program 404a may be stored in the hard disc of the server computer on the Internet, so that the computer 401 can access the server computer to download the application program 404a and install the application program 404a to the hard disc 401d.

Operating system providing graphical user interface environment such as Windows (registered trademark) manufactured and sold by US Microsoft Co. is installed in the hard disc 401d. In the following description, the application program 404a according to the present embodiment is assumed to operate on the operating system.

The input/output interface 401f is configured by serial interface such as USB, IEEE1394, RS-232C; parallel interface such as SCSI, IDE, IEEE1284; analog interface such as D/A converter, A/D converter, and the like. The keyboard 400c is connected to the input/output interface 401f, so that the user can input data to the computer 401 using the keyboard 400c.

The communication interface 401g is, for example, Ethernet (registered trademark) interface. The computer 401 transmits and receives data with the measurement unit 2 using a predetermined communication protocol by means of the communication interface 401g.

The image output interface 401h is connected to the display member 400b configured by LCD, CRT, or the like, and is configured to output an image signal corresponding to the image data provided from the CPU 401a to the display member 400b. The display member 400b displays the image (screen) according to the input image signal.

[Configuration of Each Mechanism of the Immune Analyzer]

The known configuration can be appropriately used for the configuration of each mechanism of the immune analyzer 1, and will be briefly described below.

The sample conveyance member 10 is configured to convey a rack 4 mounted with a plurality of test tubes 3 accommodating the sample to a position corresponding to an aspirating position of the sample dispensing arm 50. The sample conveyance member 10 includes a rack set section 10a for setting the rack 4 mounted with the test tube 3 accommodating un-processed sample, and a rack storage section 10b for storing the rack 4 mounted with the test tube 3 accommodating dispense processed sample. When the test tube 3 accommodating the non-processed sample is conveyed to the position corresponding to the aspirating position of the sample dispensing arm 50, the sample such as blood in the test tube 3 is aspirated by the sample dispensing arm 50, and the rack 4 mounted with the relevant test tube 3 is stored in the rack storage section 10b.

The urgent sample/tip conveyance member 20 is configured to convey the test tube 3 accommodating urgent sample that needs to be cut into the sample being conveyed by the sample conveyance member 10 for examination to an attachment position of the sample dispensing arm 50.

The pipette tip supply device 30 has a function of mounting the placed pipette tip on a tip installing section 23a of a conveyance rack 23 of the urgent specimen/tip conveyance member 20 one at a time. The tip detachment member 40 is provided to detach the pipette tip attached to the sample dispensing arm 50 to be hereinafter described.

The sample dispensing arm 50 has a function of dispensing the sample in the test tube 3 conveyed to the aspirating position by the sample conveyance member 10 into a cuvette (not shown) held by a holder 81a of a rotatable table 81 of the primary reaction member 80a to be hereinafter described. The sample dispensing arm 50 is configured to rotate an arm 51 with a shaft 52 as a center and move the arm 51 the up and down direction (Z direction). A nozzle for aspirating and discharging the sample is arranged at the distal end of the arm 51. The pipette tip conveyed by a conveyance rack (not shown) of the urgent sample/tip conveyance member 20 is attached to the distal end of the nozzle.

The reagent installing member 60a is installed with a reagent container accommodating the R1 reagent including trapped antibody and a reagent container accommodating the R3 reagent containing labeled antibody.

The reagent installing unit 60b is installed with a reagent container accommodating the R2 reagent containing magnetic particles.

The primary reaction member 80a is arranged to rotatably transport the cuvette held at the holder 81a of the rotatable table 81 by a predetermined angle for every predetermined period (20 seconds in the present embodiment), and to stir the sample, the R1 reagent, and the R2 reagent in the cuvette. That is, the primary reaction member 80a is arranged to react the R2 reagent containing magnetic particles and the antigen in the sample in the cuvette. The primary reaction member 80a is configured by the rotatable table 81 for conveying the cuvette accommodating the sample, the R1 reagent, and the R2 reagent in the rotating direction, and a container conveyance section 82 for stirring the sample, the R1 reagent, and the R2 reagent in the cuvette 8 and conveying the cuvette accommodating the stirred sample, the R1 reagent, and the R2 reagent to the primary BF separator 100a to be hereinafter described.

The container conveyance section 82 is rotatably installed at the center of the rotatable table 81. The container conveyance section 82 has a function of gripping the cuvette held at the holder 81a of the rotatable table 81 and stirring the specimen in the cuvette 8. The container conveyance section 82 also has a function of conveying the cuvette accommodating the specimen obtained by stirring and incubating the sample, the R1 reagent, and the R2 reagent to the primary BF separator 100a.

The reagent dispensing arm 90a has a function of aspirating the R1 reagent in the reagent container installed in the reagent installing member 60a, and dispensing the aspirated R1 reagent into the cuvette of the primary reaction member 80a. The reagent dispensing arm 90a is configured to rotate an arm 91b with a shaft 91c as a center, and move the arm 91b in the up and down direction. A nozzle for aspirating and discharging the R1 reagent in the reagent container is attached to the distal end of the arm 91b.

The reagent dispensing arm 90b has a function of dispensing the R2 reagent in the reagent container installed in the reagent installing member 60b into the cuvette dispensed with the sample and the R1 reagent of the primary reaction member 80a. The reagent dispensing arm 90b is configured to turn an arm 92b with the shaft 92c as the center, and move the arm 92b in the up and down direction (Z direction). A nozzle for aspirating and discharging the R2 reagent in the reagent container is attached to the distal end of the arm 92b.

In the present embodiment, the primary BF separator 100a is arranged to separate the non-reactive R1 reagent (unnecessary component) and the magnetic particles from the specimen in the cuvette conveyed by the container conveyance section 82 of the primary reaction member 80a.

The cuvette of the primary BF separator 100a separated with the non-reactive R1 reagent etc. is conveyed to the holder 83a of the rotatable table 83 of the secondary reaction member 80b by the conveyance mechanism 96. The conveyance mechanism 96 is configured to turn an arm 96a including a cuvette gripping part (not shown) at the distal end with a shaft 96 as the center, and move the arm 96a in the up and down direction (Z direction).

The secondary reaction member 80b has a configuration similar to the primary reaction member 80a, and is arranged to rotatably transport the cuvette held at the holder 83a of the rotatable table 83 by a predetermined angle for every predetermined period (20 seconds in the present embodiment), and to stir the sample, the R1 reagent, the R2 reagent, the R3 reagent, and the R5 reagent in the cuvette. That is, the secondary reaction member 80b is arranged to react the R3 reagent including labeled antibody and the antigen in the sample in the cuvette, and to react the R5 reagent having luminescent substrate and the labeled antibody of the R3 reagent. The secondary reaction member 80b is configured by the rotatable table 83 for conveying the cuvette 8 accommodating the sample, the R1 reagent, the R2 reagent, the R3 reagent and the R5 reagent in the rotating direction, and a container conveyance section 84 for stirring the sample, the R1 reagent, the R2 reagent, the R3 reagent and the R5 reagent in the cuvette and conveying the cuvette accommodating the stirred sample etc. to the secondary BF separator 100b to be hereinafter described. Furthermore, the container conveyance section 84 has a function of again conveying the cuvette processed by the secondary BF separator 100b again to the holder 83a of the rotatable table 83.

The reagent dispensing arm 90c has a function of aspirating the R3 reagent in the reagent container installed at the reagent installing member 60a and dispensing the aspirated R3 reagent into the cuvette dispensed with the sample, the R1 reagent, and the R2 reagent of the secondary reaction member 80b. The reagent dispensing arm 90c is configured to turn the arm 93b with the shaft 93c as the center, and move the arm in the up and down direction. A nozzle for aspirating and discharging the R3 reagent in the reagent container is attached to the distal end of the arm 93b.

The secondary BF separator 100b has a configuration similar to the primary BF separator 100a, and is arranged to separate the non-reactive R3 reagent (unnecessary component) and the magnetic particles from the specimen in the cuvette conveyed by the container conveyance section 84 of the secondary reaction member 80b.

A R4 reagent supply section 94 and a R5 reagent supply section 95 are respectively arranged to supply the R4 reagent and the R5 reagent, respectively, to the cuvette held at the holder 83a of the rotatable table 83 of the secondary reaction member 80b.

The detector 120 is arranged to measure the amount of antigen contained in a sample by acquiring the light generated in the reaction process of the labeled antibody bound to the antigen of the sample performed with a predetermined process and the luminescent substrate with a photo multiplier tube.

The detector 120 includes a conveyance mechanism section 121 for conveying the cuvette held at the holder 83a of the rotatable table 83 of the secondary reaction member 80b to the detector 120.

The used cuvette aspirated with the measured specimen is discarded to a dust box (not shown) arranged at the lower part of the immune analyzer 1 through a discarding hole 130.

[Overall Process]

Figure 4:
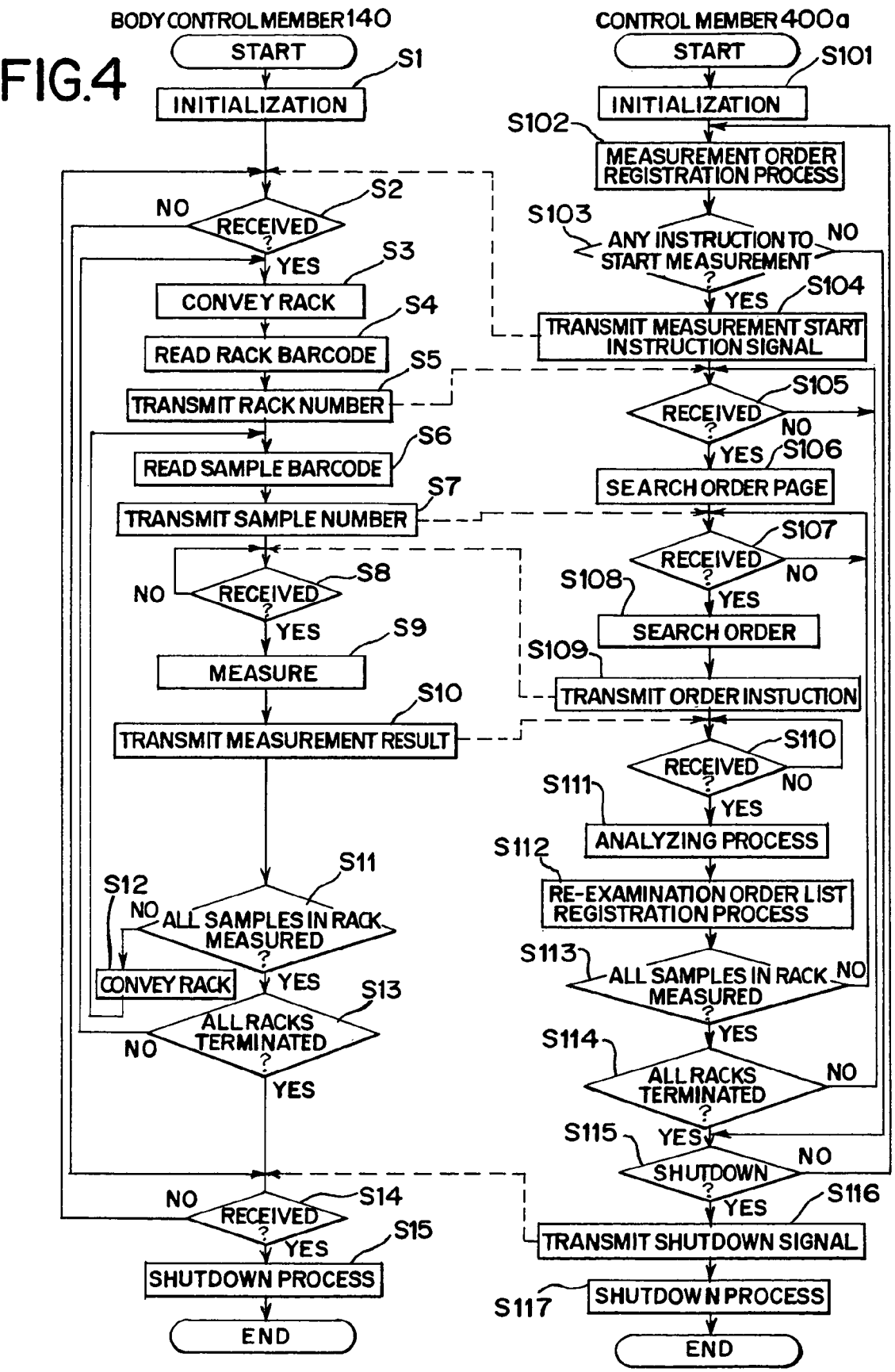
FIG. 4 is a view showing an overall flow of immune analysis using the immune analyzer shown in FIG. 1.

The overall flow of the analyzing process by the immune analyzer 1 is shown in FIG. 4. In the determination in the flowchart below, if "Yes" and "No" are not shown, the downward arrow means Yes, and the right (left) arrow means No. The process described below is the process controlled by the control member 400a or the body control member 140.

First, when the power of the immune analyzer 1 is turned ON, initialization of the body control member 140 is performed (step S1). In the initialization operation, initialization of the program, return to original position of the drive portion of the immune analyzer 1, and the like are performed.

When the power of the personal computer 401 communicatably connected to the immune analyzer 1 is turned ON, on the other hand, initialization of the control member 400a of the personal computer 401 is performed (step S101). In the initialization operation, initialization of the program and the like are performed. After initialization is completed, order registration of the sample for performing analysis using the immune analyzer 1 is accepted (function serving as order receiving means; step S102). The order registration is performed by having the user input information such as sample number and measurement item from the keyboard (input means) 400c, and after checking the content, having the user operate (click) the instruction button of order registration.

The order registration executed by the control member 400a is stored in a storage region of the hard disc 401d. The order registration includes registration on the sample to be analyzed for the first time and registration performed by the user based on the re-examination order list (see step S112) to be hereinafter described on the sample for performing re-examination.

In step S103, the control member 400a determines whether or not instruction to start the measurement is made. The control member 400a proceeds to the process to step S104 when determining that instruction to start the measurement is made (Yes), and proceeds to process to step S115 when determining that instruction to start the measurement is not made (No). In step S104, the control member 400a transmits the measurement start signal to the body control member 140.

In step S2, the body control member 140 determines whether or not the measurement start signal is received. The body control member 140 proceeds the process to step S3 when determining that the measurement start signal is received (Yes), and proceeds the process to step S14 when determining that the measurement start signal is not received (No).

In step S3, the sample conveyance member 10 conveys the rack 4 mounted with a plurality of tubes containing the sample to a position corresponding to the aspirating position 1a of the sample dispensing arm 50. The rack 4 is given a barcode or recording part recorded with information (rack number) specifying the rack 4, which barcode is read by a detector (not shown) arranged on a conveyance path for conveying the rack to a predetermined position (step S4). The read rack number is transmitted to the personal computer 401 by the body control member 140 in step S5.

In step S105, the control member 400a determines whether or not the rack number is received. The control member 400a proceeds the process to step S106 when determining that the rack number is received (Yes).

In step S106, the control member 400a searches the order page. In other words, the control member 400a searches for the order information related to the rack number received in step S104 from the order information stored in the storage region of the hard disc 401d.

A barcode or the recording part recorded with information (sample number) for specifying the sample in the test tube 3 is attached to the test tube 3 similar to the rack 4, which barcode is read by a detector (not shown) arranged on a conveyance path for conveying the rack 4 mounted with the test tube 3 to a predetermined position (Step S6). In step S7, the read sample number is transmitted to the personal computer 401. The barcodes of the test tube 3 and the rack 4 may be read by different detector or may be read by a common detector.

In step S107, the control member 400a determines whether or not the sample number is received. The control member 400a proceeds the process to step S108 when determining that the sample number is received (Yes).

In step S108, the control member 400a searches the order. In other words, the control member 400a searches for the order information related to the sample number received in step S107 from the order information related to the specific rack number searched in step S106. In step S109, the control member 400a transmits the instruction of order to the body control member 140.

In step S8, the body control member 140 determines whether or not the order instruction is received. The body control member 140 proceeds the process to step S9 when determining that the order instruction is received (Yes).

In step S9, measurement on the ordered item is performed. The measurement result is transmitted from the body control member 140 to the personal computer 401 side (Step S10).

In step S110, the control member 400a determines whether or not the measurement result is received. The control member 400a proceeds the process to step S111 when determining that the measurement result is received (Yes).

In step S111, analyzing process of the measurement result transmitted from the body control member 140 side is performed. In other words, the control member 400a converts the concentration of the antigen to be measured from the transmitted measurement result and the analytical curve created using a standard specimen in advance and stored in the hard disc 401d, and stores the result (analysis result). The control member 400a also outputs the analysis result.

In step S112, the order list of the sample requiring re-analysis or re-measurement is registered based on the analysis result obtained in step S111. The re-analysis is performed when the measurement result of the sample takes a value outside a predetermined range, when useful measurement result is not obtained due to measurement error (skip of measurement of a specific item due to lack of reagent, stop of measurement member by immediate stop error), and the like.

In step S113, the control member 400a determines whether or not the measurement is performed on the samples in all the test tubes 3 held at the racks 4. The control member 400a proceeds the process to step S114 when determining that the measurement is performed on the samples in all the test tubes 3 held at the racks 4 (Yes), and returns the process to step S107 when determining that the measurement is not performed on the samples in all the test tubes 3 held at the racks 4 (No).

In step S114, the control member 400a determines whether or not the measurement is performed on all the racks 4. The control member 400a proceeds the process to step S115 when determining that the measurement is performed on all the racks 4 (Yes), and returns the process to step S105 when determining that the measurement is not performed on all the rack 4 (No).

In step S115, the control member 400a determines whether or not an instruction to shutdown the personal computer 401 is received. The control member 400a proceeds the process to step S116 when determining that the instruction to shutdown is received (Yes), and returns the process to step S102 when determining that the instruction to shutdown is not received (No).

In step S116, the control member 400a transmits a shutdown signal to the body control member 140.

In step S117, the control member 400a shuts down the personal computer 401, and the process is terminated.

In step S11, the body control member 140 determines whether or not the measurement is performed on the samples in all the test tubes 3 held at the rack 4. The body control member 140 proceeds the process to step S13 when determining that the measurement is performed on the samples in all the test tubes 3 held at the rack 4 (Yes), and conveys the rack 4 by a predetermined distance (distance for the test tube containing the sample to be measured next to reach the position to be aspirated) (step S12) when determining that the measurement is not performed on the samples in all the test tubes 3 held at the rack 4 (No), and returns the process to step S6.

In step S13, the body control member 140 determines whether or not the measurement is performed on all the racks 4. The body control member 140 proceeds the process to step S14 when determining that the measurement is performed on all the racks 4 (Yes), and returns the process to step S3 when determining that the measurement is not performed on all the racks 4 (No).

In step S14, the body control member 140 determines whether or not the shutdown signal is received. The body control member 140 proceeds the process to step S15 when determining that the shutdown signal is received (Yes), and returns the process to step S2 when determining that the shutdown signal is not received (Yes).

In step S15, the body control member 140 shuts down the immune analyzer 1, and the process is terminated.

[Measurement Count History Screen]

The immune analyzer 1 of the present embodiment has a function of counting the number of measurements (number of analysis) by type of measurement (type of analysis) and by measurement items (analyzing items) for the measurements performed in a predetermined period, specifically, one month and one day. The analyzer also has a function of displaying the counted number of measurements on the display member 400b. These functions will be described below.

Figure 7:
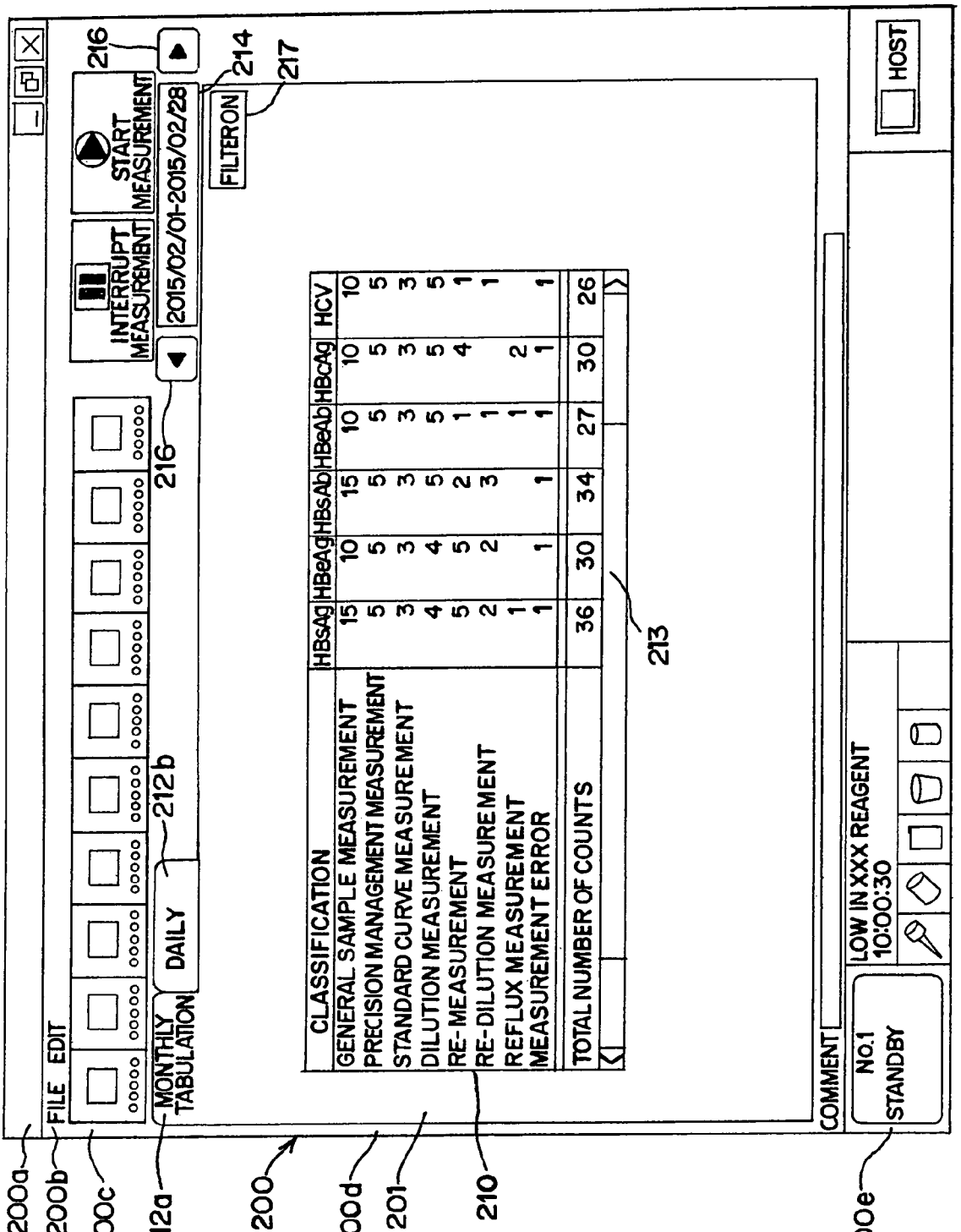
FIG. 7 is a view showing the measurement count history screen.

FIGS. 7 and 8 are views showing a measurement count history screen 201 displayed on the display member 400b. The measurement count history screen 201 is displayed on a main window 200. The main window 200 includes a title bar 200a, a menu bar 200b, a tool bar 200c, a main display zone 200d, and an auxiliary display zone 200e, where the measurement count history screen 201 is displayed on the main display zone 200d. The measurement count history screen 201 can be activated by operating the menu bar 200b or the tool bar 200c.

The measurement count history screen 201 is displayed with a table 210 (FIG. 7), 211 (FIG. 8) summarizing the total of the number of measurements for every month or every day by measurement type (classification) and by measurement item. FIG. 7 shows an example displaying the table 210 of "monthly total" or total of every month, and FIG. 8 shows an example displaying the table 211 "daily" or total of every day. The switch of display between "monthly total" and "daily" is performed by selecting tabs 212a, 212b.

In FIG. 7, eight types of measurements "general sample measurement", "precision management measurement", "standard curve measurement", "dilution measurement", "re-measurement", "re-dilution measurement", "reflux measurement", and "measurement error" are listed in the column of "classification" at the left end of the table 210.

Of the types of measurement, "general sample measurement" is a general measurement performed first on the sample obtained from the patient. The number of measurements from which result is obtained other than "precision management measurement", "standard curve measurement", "dilution measurement", "re-measurement", "re-dilution measurement", and "reflux measurement" is displayed therebelow in the row of general sample measurement.

"Precision management measurement" is a measurement performed to determine whether a constant analysis precision can be obtained by measuring the precision management specimen same as or similar to the biological sample, and monitoring the measurement result, and is performed once a day. "Standard curve measurement" is a measurement of the calibrator performed to create a standard curve. Such measurements are measurements related to maintaining the examination precision, and are not measurements for measuring the sample of the patient.

"Re-measurement" is a measurement performed under the same condition for the same measurement item when the measurement result of the general sample measurement takes a value outside the predetermined range, or when the useful measurement result is not obtained due to measurement error. "Dilution measurement", "re-dilution measurement", and "reflux measurement" are re-measurement (re-analysis) performed after the general sample measurement, where "dilution measurement" is the re-measurement performed with the specimen diluted when the measurement result other than the predetermined range is obtained, "re-dilution measurement" is the re-measurement performed while changing the dilution magnification, and "reflux measurement" is the re-measurement performed on the measurement item different from the above measurement item according to a predetermined rule when a certain measurement item takes an abnormal value in the general sample measurement.

"Measurement error" refers to an error of when the measurement order is accepted but the measurement result is not obtained due to reasons of operation failure of the device, lack of amount of reagent, and the like. The measurement result is a value reflecting the aspect of the sample obtained when the measurement is normally terminated, and refers to both quantitative result and qualitative result.

The immune analyzer 1 of the present embodiment can perform nine items of "HBsAg", "HBeAg", "HBsAb", "HBeAb", "HBcAb", "HCV", "HIV", "HTLV", "TP" for the measurement items on infective disease, and three items of "TSH", "FT3", "FT4" for the measurement items on hormone, such measurement items name being displayed in a line on a first row of the table 210. In the illustrated example, only six measurement items are displayed on the table 210, but the remaining items can be displayed by operating the scroll bar 213.

The row "total number of counts" is provided at the bottom of the table 210, where the numerical value adding up the number of measurements for one month is displayed by measurement item for all types of measurement in the row of total number of counts.

In FIG. 8, a column displaying the date is provided at the left end of the table 211 of "daily", and eight types of measurements "general sample measurement", "precision management measurement", "standard curve measurement", "dilution measurement", "re-measurement", "re-dilution measurement", "reflux measurement", and "measurement error" are listed for each date, so that the number of measurements is displayed by measurement item for each measurement type.

In FIGS. 7 and 8, a total period 214 of the number of measurement currently displayed is shown at the upper right of the tables 210, 211 of the measurement count history screen 201. In the illustrated example, "2015/02/01-2015/02/28" is displayed, which means that the total of February of 2015 is displayed in the table 210 of "monthly total", and the total by day between February 1to 28 of 2015 is displayed in the table 211 of "daily". That is, in the monthly total, the counting period or the unit period of counting the number of measurements matches the total period, and the number of measurements during the total period is counted by measurement item and by measurement type. In the daily total, the counting period is one day and differs from the total period (one month in default), where the total period is divided by the counting period, and the number of measurements is counted by the measurement item and by the measurement type in each counting period. Only the display from February $1^{st}$ to $3^{rd}$ is displayed on FIG. 8, but up to $28^{th}$ can be displayed by operating the scroll bar 215.

A display feed button 216 is displayed on both sides of the total period 214, where the tables 210, 211 of "monthly total" or "daily" of the previous month or the next month can be displayed by selecting (clicking) the display feed button 216.

Figure 9:
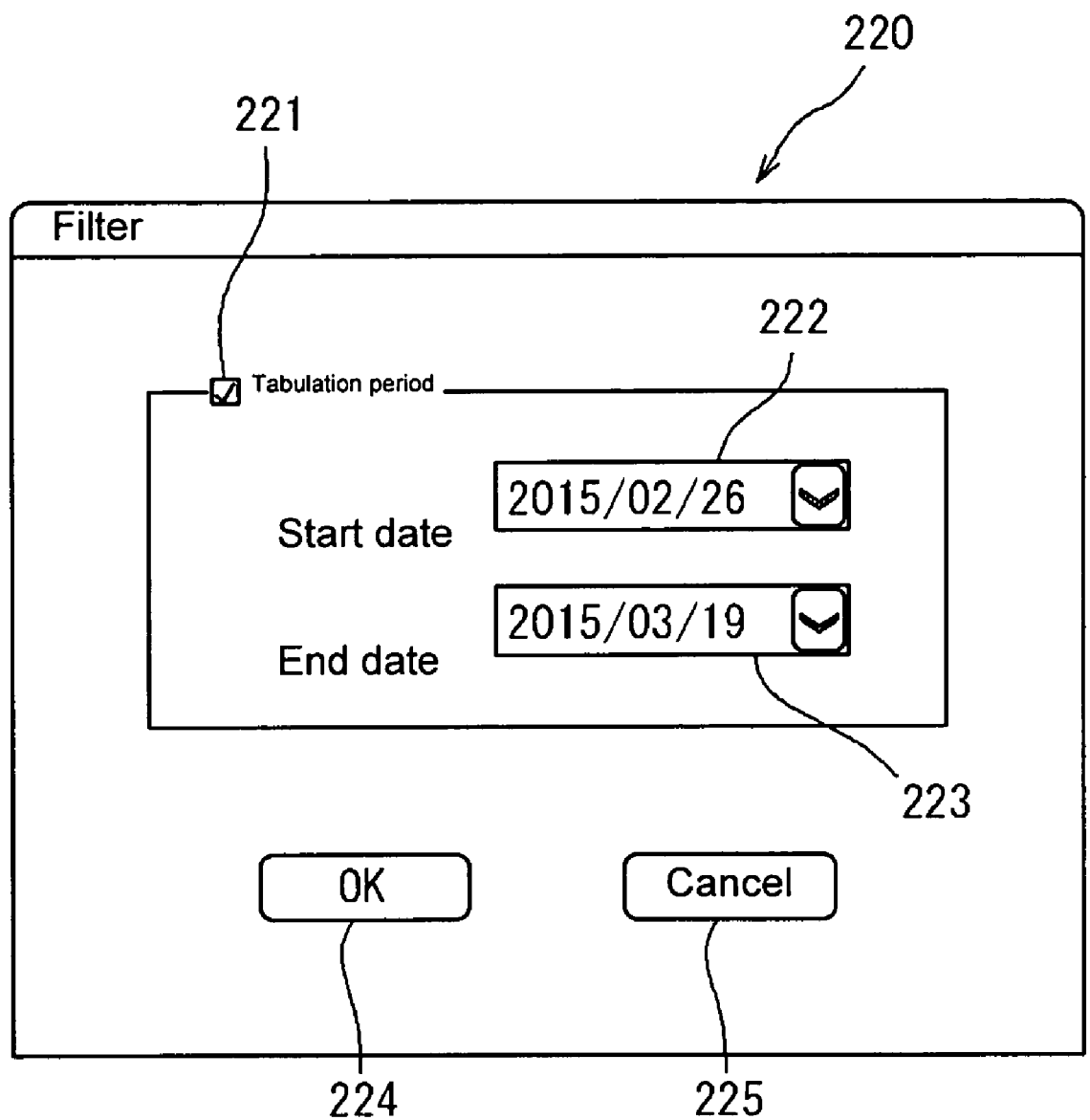
FIG. 9 is a view showing a filter dialogue.

As shown in FIGS. 7 and 8, "filter ON" button 217 is displayed on the right side of the table 210, 211. When the "filter ON" button 217 is selected, a filter dialogue 220 as shown in FIG. 9 is displayed. The filter dialogue 220 is provided to arbitrarily designate the total period in the monthly total, and includes a check box 221 for selecting whether or not to designate the total period, a start date input area 222 for selecting and inputting the start date of the total period with a pull-down menu, and an end date input area 223 for selecting and inputting the end date of the total period with a pull-down menu. When the check box 221 is not selected, the total period is set with a period from the first date to the last date of the month. The user can select the check box 221, input the start date and the end date of the total period, and push the "OK" button 224 to designate the total period. In the immune analyzer 1 of the present embodiment, the total accumulating period of the number of measurements is set to fifteen months, and the pull-down menu of the start date input area 222 and the end date input area 223 is set so that the months and dates for fifteen months can be selected.

When the total period is designated by the filter dialogue 220, the measurement result of the number of measurements performed during the relevant total period is displayed by measurement type and by measurement item on the screen of "monthly total", and the measurement result of the number of measurements in each date during the period is displayed by measurement type and by measurement item on the screen of "daily" (same mode as tables 210, 211 of FIGS. 7 and 8, different total period 214). That is, the counting period of the monthly total is variable, and the user can change the period to a desired period. The counting period (one day) of the total by date is fixed, and the counting is performed every day throughout the entire total period.

[Display Process of Measurement Count History Screen]

The process of displaying the measurement count history screen will now be described.

Figure 5:
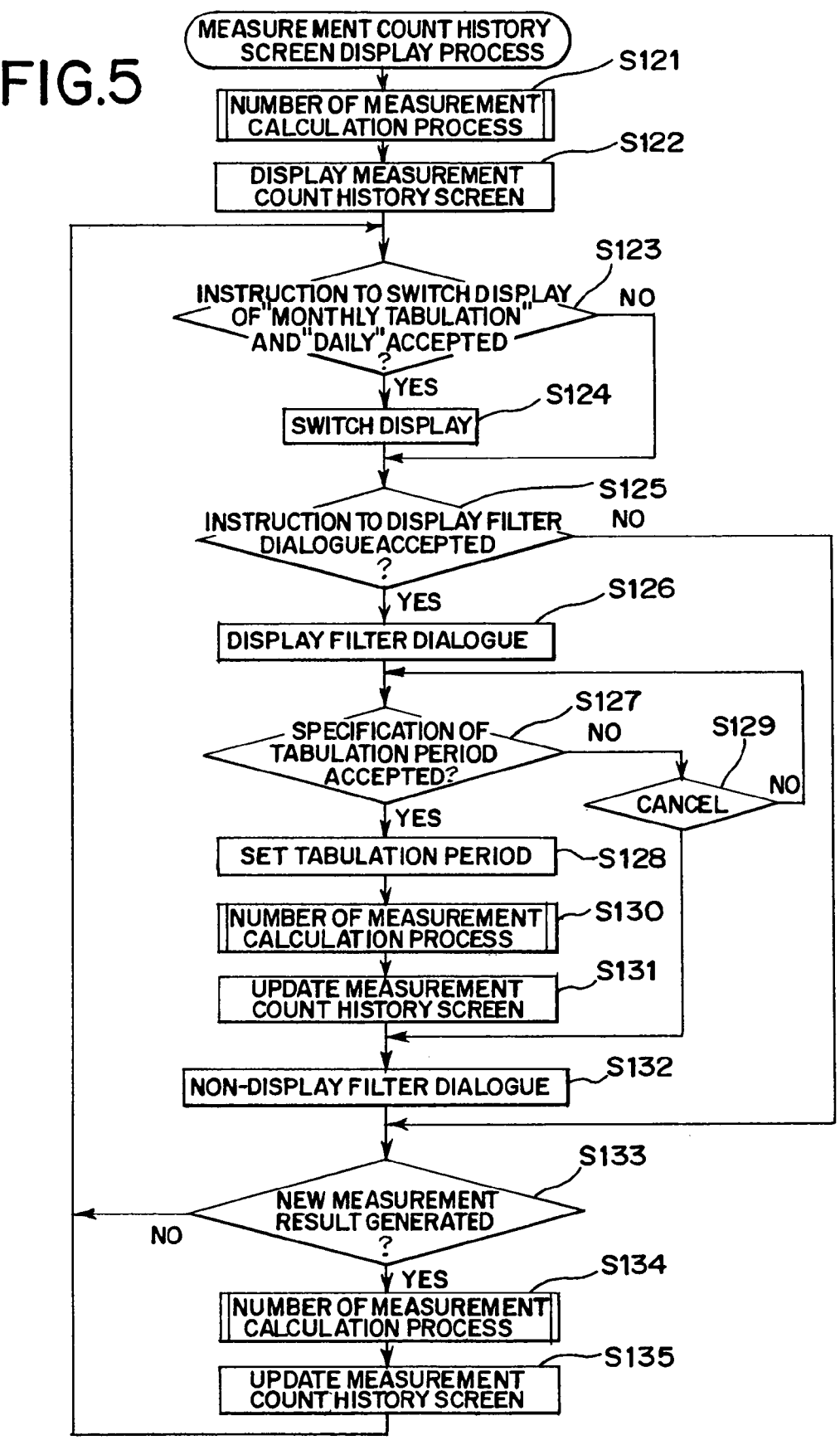
FIG. 5 is a flowchart showing a processing procedure of a measurement count history screen display process.

FIG. 5 is a flowchart showing a processing procedure for displaying the measurement count history screen on the display member 400b. In step S121, the control member 400a first performs a number of measurement calculation process of totalizing the number of measurements for one month and one day by measurement type and by measurement item. The number of measurement calculation process will be hereinafter described in detail.

In step S122, the control member 400a displays the measurement count history screen 201 as shown in FIG. 7 or FIG. 8 on the display member 400b. In the initial state, the "monthly total" screen of FIG. 7 is displayed.

In step S123, the control member 400a determines whether or not an instruction to switch the display of "monthly total" or "daily", that is the selection of tab 212a, 212b in FIG. 7 and FIG. 8 is accepted. If the instruction to switch the display of "monthly total" or "daily" is accepted (Yes), the control member 400a switches the display in step S124, and proceeds the process to step S125. If the instruction to switch the display of "monthly total" or "daily" is not accepted (No), the control member 400a proceeds the process to step S125.

In step S125, the control member 400a determines whether or not an instruction to display the filter dialogue 220, that is, selection of "filter ON" button 214 of FIG. 7 and FIG. 8 is accepted. The control member 400a displays the filter dialogue 220 on the display member 400b (step S126) if the instruction to display the filter dialogue 220 is accepted (Yes), and proceeds the process to step S133 if the instruction is not accepted (No).

In step S127, the control member 400a determines whether or not specification of the total period is accepted in the filter dialogue 220 (whether selection of the check box 221 of the filter dialogue 220 in FIG. 9, input of start date and end date, and selection of "OK" button 224 is made), and proceeds the process to step S128 if accepted (Yes), and proceeds the process to step S129 if not accepted (No).

In step S128, the control member 400a sets the total period, and again performs the number of measurement calculation process for the relevant total period (step S130). The number of measurement calculation process is a process substantially the same as the process performed in step S121, and the details will be hereinafter described in detail.

In step S129, the control member 400a determines whether or not "cancel" button 225 (see FIG. 9) is selected in the filter dialogue 220, and proceeds the process to step S132 if the button 225 is selected and returns the process to step S127 if not selected.

In step S131, the control member 400a updates the measurement count history screen 201 according to the set total period.

In step S132, the control member 400a non-displays the filter dialogue 220.

In step S133, the control member 400a determines whether or not a new measurement result is generated, and proceeds the process to step S134 if the new measurement result is generated (Yes), and returns the process to step S123 if not generated (No).

If the new measurement result is generated, the control member 400a performs the number of measurement calculation process in step S134. This number of measurement calculation process is the same as the process performed in step S121, and the details will be hereinafter described.

In step S135, the control member 400a updates the measurement count history screen 201 and returns the process to step S123.

[Number of Measurement Calculation Process]

Figure 6:
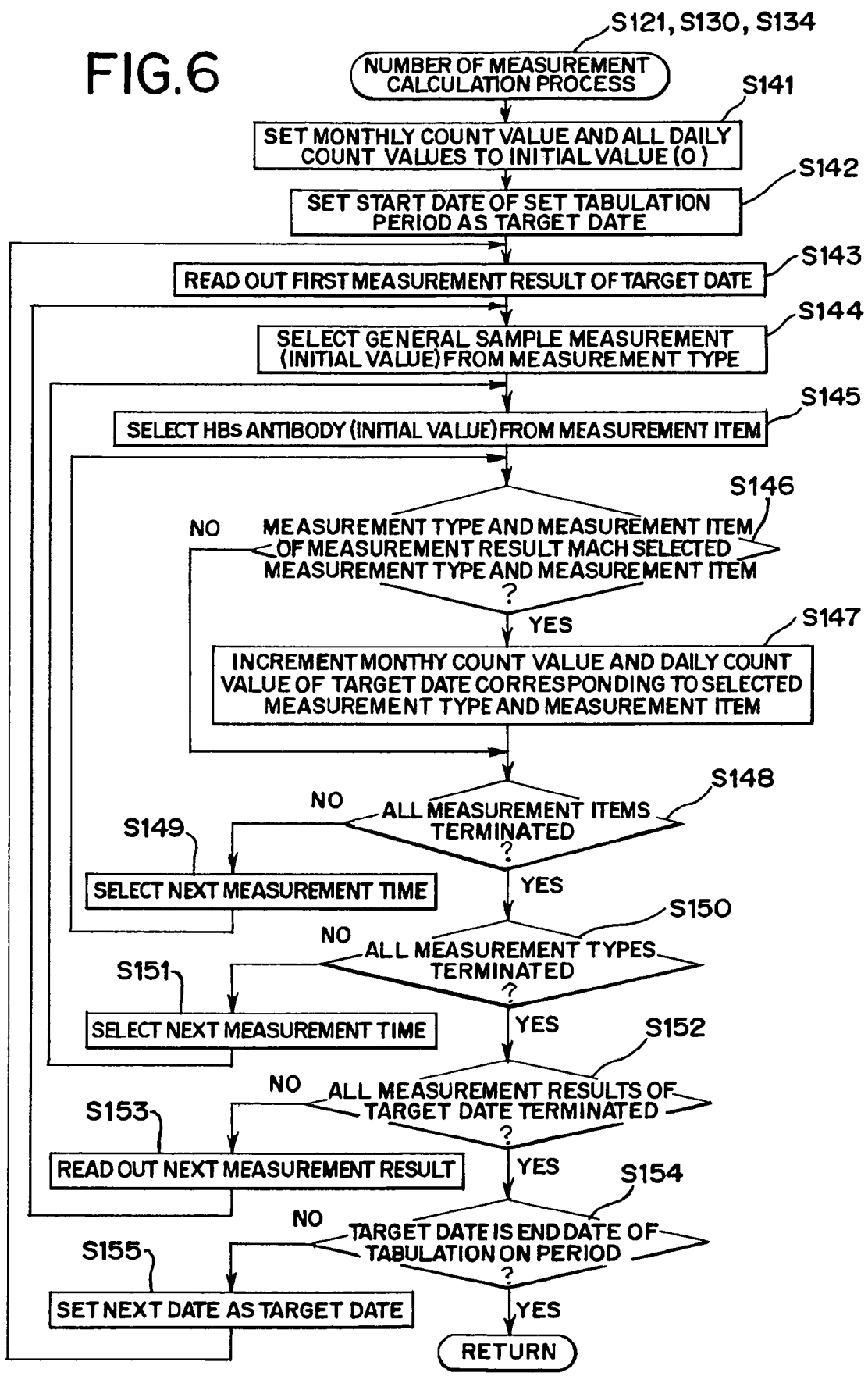
FIG. 6 is a flowchart showing a processing procedure of the number of measurement calculation process.

The number of measurement calculation process performed in steps S121, S130, S134 of FIG. 5 will be described. FIG. 6 is a flowchart showing a processing procedure of the number of measurement calculation process. In step S141 of FIG. 6, the control member 400a sets the "monthly count value" and all the "daily count value" to an initial value (0). The "monthly count value" is a variable of the number of measurement counts for one month, and is set for every combination of the measurement type and the measurement item. The "daily count value" is a variable of the number of measurement counts for one day, and is set for every combination of the measurement type and the measurement item. The daily count value is set for each day during the total period.

In step S142, the control member 400a sets the start date of the total period to "target date" serving as the target of the count. The start date is, for example, the first day of the month (February $1^{st}$ in the example shown in FIGS. 7 and 8) when performing the monthly total and the daily total. The start date is the start date of the total period if the total period is designated by the filter dialogue 220.

In step S143, the control member 400a reads out the first measurement result of the measurements performed on the "target date" from the hard disc 401d.

In step S144, the control member 400a selects the measurement type that becomes the initial value from the measurement types. For instance, when performing the number of measurement calculation process in the order lined in the column of "classification" of FIG. 7, "general sample measurement" is selected for the initial value.

In step S145, the control member 400a selects the measurement item that becomes the initial value from the measurement types. For instance, when performing the number of measurement calculation process in the order lined in the row of the measurement item name of FIG. 7, "HBsAg" is selected for the initial value.

In step S146, the control member 400a determines whether or not the measurement type and measurement item in the first measurement result performed on the "target date" match the selected measurement type and measurement item. That is, here, determination is made on whether or not the first measurement on the target date is the result of "general sample measurement" and includes the measurement result of "HBsAg". If the measurement type and the measurement item of the first measurement result of the target date match the selected measurement type and measurement item (Yes), the control member 400a increments the "monthly count value" and the "daily count value" corresponding to the selected measurement type ("general sample measurement" herein) and the measurement item ("HBsAg" herein) in step S147, and proceeds the process to step S148. Since whether or not the measurement result is included is determined in step S146, the measurement in which the analyzing order is accepted but the measurement result is not obtained (i.e., in the case of measurement error), the count value is not incremented. If the measurement type is the measurement error, the "monthly count value" and the "daily count value" are incremented when the analyzing order is accepted but the measurement result is not obtained.

If the first measurement result of the target date is not "general sample measurement" and "HBsAg" (No) in step S146, the control member 400a proceeds the process to step S148.

In step S148, the control member 400a determines whether or not the counting for all the measurement items is terminated in the selected measurement type ("general sample measurement" herein), and proceeds the process to step s150 if terminated (Yes) and proceeds the process to step S149 if not terminated (No).

In step S149, the next measurement item (second "HBeAg") in the selected measurement type ("general sample measurement" herein) is selected, and the process is returned to step S146. The processes (step S146 to S149) similar to the above are repeatedly performed until the counting on all the measurement items in the selected measurement type ("general sample measurement") is terminated.

In step S150, the control member 400a determines whether or not the counting for all the measurement types is terminated. The control member 400a proceeds the process to step S152 if the counting for all the measurement types is terminated (Yes), and proceeds the process to step S151 if not terminated (No).

The control member 400a selects the next measurement type (second "precision management measurement" herein) in step S151, and returns the process to step S145 to select the measurement item (first "HBsAg") that becomes the initial value. The processes (steps S145 to S151) similar to the above are repeatedly performed until the counting on all the measurement types and all the measurement items are terminated.

The control member 400a determines whether or not the counting on all the measurement results of the "target date" (start date herein) is terminated in step S152. The control member 400a proceeds the process to step S154 when the counting on all the measurement results is terminated (Yes), and proceeds the process to step S153 if not terminated (No).

In step S153, the control member 400a newly reads out the next measurement result on the same target date from the hard disc 401d, returns the process to step S144, and repeatedly performs the processes (steps S144 to S153) similar to the above until the counting on all the measurement types and measurement items is terminated for the measurement result. That is, the processes of step S144 to step S153 are repeated until the measurement error is selected as the measurement type, and the counting on all the analyzing items is terminated.

In step S154, the control member 400*a* determines whether or not the "target date" is the end date of the total period, and returns the process if the target date is the end date (Yes), and proceeds the process to step S155 if not the end date (No). In step S155, the control member 400*a* sets the "target date" as the next date, returns the process to step S143, and repeatedly performs the processes (steps S143 to 155) similar to the above for all the measurement types and all the measurement times until the "target date" reaches the final date of the total period.

According to the above processes, the counting of the number of measurements during the total period and the counting of the number of measurements for every day during the total period are performed, and the total result can be displayed on the display member 400*b*. Furthermore, the total result can be output on paper in a table form through a printer (not shown) connected to the control device 400. The total result can be read out using a general spreadsheet software, a text editor, and the like, and output to the hard disc 401*d* in a file (CSV file format etc.) of a format that can be processed or printed. The total data can be automatically transmitted to a computer connected to the control device 400*a* through a communication network. Such total data may be automatically or manually transmitted to the computer on the maintenance service side via the network, so that the usage state of the immune analyzer 1 can be understood without the maintenance service side going to the institution of the user.

[Use of Measurement Count History]

In the present embodiment, the number of measurements is counted in two different counting periods of one month (or designated total period) and one day, and the number of measurements is totalized, and thus the total result can be displayed in various patterns according to the usage purpose, and such total results can be used for research of the operating state of the immune analyzer 1 and various managements of the analyzer.

The total number of measurements for every plurality of types of counting period can also be used to manage consumable goods of the immune analyzer 1. In the present embodiment, the number of measurements performed in one month and one day is totalized by measurement item, and thus the amount of reagent etc. consumed in each period can be obtained, and the future consuming amount of the consumable goods can be appropriately predicted to be used for inventory control.

In the present embodiment, the sample which analyzing order is accepted but the measurement result is not obtained is not included in the "general sample measurement", but such sample may be counted as the number of measurement of the "general sample measurement". In this case, the count value of "measurement error" is subtracted from the count value of the "general sample measurement" to acquire the number of times the measurement result is obtained, and the calculation of the utility rate corresponding to the number of measurements can be appropriately performed.

The embodiment disclosed herein is merely illustrative in all aspects and should not be recognized as being restrictive. The scope of the invention is defined by the scope of the claims rather than by the description of the embodiment, and meaning equivalent to the claims and all modifications within the scope is encompassed herein.

For instance, a configuration of counting the number of analyses of the immune analyzer by analyzing item and analyzing type, and displaying the counted result has been described in the present embodiment, but is not limited thereto, and a configuration of counting the number of analyses of apparatuses other than the immune analyzer such as gene amplification measurement apparatus, blood coagulation measurement apparatus, and multiple blood cell analyzer, and displaying the counted result may be adopted.

In the present embodiment, the monthly total is displayed on the measurement count history screen 201 in the initial state, and the number of measurements of the total period designated in the filter dialogue 220 is displayed on the measurement count history screen 201 when the "filter ON" button 217 is selected. However, the present invention is not limited thereto, and both the monthly total and the filter dialogue 220 may be displayed on the measurement count history screen 201 in the initial state.

The invention claimed is:

1. A sample analyzer comprising:
a measurement sample preparation section;
an analyzing section;
an outputting device;
a controller having a processor and a memory programmed to perform instructions comprising steps of:
receiving order information indicating a predetermined measurement item on which analysis is to be performed on a biological sample;
controlling the measurement sample preparation section to mix the biological sample and a reagent so as to prepare a measurement sample in accordance with the order information; and
controlling the analyzing section to analyze the measurement sample, an analysis of the measurement sample being performed for one of predetermined types to determine on the predetermined measurement item;
wherein the controller is further programmed to perform instruction comprising steps of:
counting a first number of analysis for the predetermined measurement item by the analyzing section during a first counting period, and counting a second number of analysis for the predetermined measurement item -by the analyzing section during a second counting period different from the first counting period;
wherein the step of counting comprises repeating counting the first number of analysis for the predetermined measurement item until counting for the predetermined measurement item with respect to each and every predetermined measurement type is completed during the first counting period; and
repeating counting the second number of analysis for the predetermined measurement item until counting for the predetermined measurement item with respect to each and every predetermined measurement type is completed during the second counting period;
receiving a selection of one of the first counting period and the second counting period; and
outputting to the outputting device the first number of analysis, or the second number of analysis associated with a selected counting period, the step of outputting further comprises:
switching a display of the first number of analysis to a display of the second number of analysis associated with the selected counting period;
displaying a table showing the first number of analysis, or the second number of analysis with respect to the predetermined measurement item and each and every predetermined measurement type; and displaying a filter button that prompts a filter dialogue that allows a user to designate an arbitrary counting period within one of the first counting period and the second counting period.

2. The sample analyzer according to claim 1, wherein the controller is further programmed to perform an instruction comprising the step of counting a total number of times that the first number of analysis or the second number of analysis is obtained.

3. The sample analyzer according to claim 1, wherein the controller is further programmed to perform an instruction comprising the step of counting a total number of times that the order information is received but no measurement result of the biological sample is obtained.

4. The sample analyzer according to claim 1, wherein
the order information further comprises predetermined measurement type information indicating whether an analysis to be performed on the biological sample is a general sample measurement or a re-measurement;
the controller is further programmed to perform instructions comprising the steps of:
counting a third number of analysis of the general sample measurement and a fourth number of analysis of the re-measurement during the first counting period; and
counting a fifth number of analysis of the general sample measurement and a sixth number of analysis of the re-measurement during the second counting period; and
outputting either the third number and the fourth number, or the fifth number and the sixth number based on the selected counting period.

5. The sample analyzer according to claim 1, further comprising:
the controller is further programmed to perform instructions comprising the steps of:
changing the second counting period; and
counting the second number of analysis during the changed second counting period.

6. The sample analyzer according to claim 1, wherein the first counting period is a fixed period.

7. The sample analyzer according to claim 1, further comprising:
a display device; and
wherein the controller is further programmed to perform an instruction comprising the step of controlling the display device to display the first number of analysis, or the second number of analysis associated with the selected counting period.

8. A sample analyzer comprising:
a measurement sample preparation section;
an analyzing section;
an outputting device;
a controller having a processor and a memory programmed to perform instructions comprising steps of:
receiving order information indicating a predetermined measurement item on which analysis is to be performed on a biological sample;
controlling the measurement sample preparation section to mix the biological sample and a reagent so as to prepare a measurement sample in accordance with the order information; and
controlling the analyzing section to analyze the measurement sample, an analysis of the measurement sample being associated with the predetermined measurement item and one of a plurality of predetermined measurement types;
wherein the controller is further programmed to perform instruction comprising steps of:
receiving designation of an arbitrary counting period;
counting a number of analysis for the predetermined measurement type during a received designated counting period;
wherein the step of counting comprises repeating counting the number of analysis for one of the predetermined measurement types until counting for one of the predetermined measurement types with respect to each and every predetermined measurement item of plural predetermined measurement items is completed during the received designated counting period;
outputting to the outputting device the number of analysis associated with the received designated counting period, the step of outputting further comprises:
displaying a table showing the number of analysis with respect to a predetermined measurement type and each and every measurement item during the received designated counting period; and
displaying a filter button that prompts a filter dialogue that allows a user to designate the arbitrary counting period.

9. The sample analyzer according to claim 8, wherein the controller is further programmed to perform an instruction comprising the step of counting a total number of times that the number of analysis is obtained.

10. The sample analyzer according to claim 8, wherein the controller is further programmed to perform an instruction comprising the step of counting a number of times that the order information is received but a measurement result is not obtained.

11. The sample analyzer according to claim 8, wherein the order information further comprises predetermined measurement type information indicating whether an analysis to be performed on the biological sample is a general sample measurement or a re-measurement; and
the controller is further programmed to perform instructions comprising the steps of:
receiving order information of the general sample measurement and the re-measurement;
counting a number of analysis of the general sample measurement and a number of analysis of the re-measurement during the received designated counting period; and
outputting the number of analysis of the general sample measurement and the number of analysis of the re-measurement during the received designated counting period.

12. A sample analyzer comprising:
a measurement sample preparation section;
an analyzing section;
an outputting device;
a controller having a processor and a memory programmed to perform instructions comprising steps of:
receiving order information indicating a predetermined measurement item on which analysis is to be performed on a biological sample;
controlling the measurement sample preparation section to mix the biological sample and a reagent so as to prepare a measurement sample in accordance with the order information; and
controlling the analyzing section to analyze the measurement sample, an analysis of the measurement sample being associated with the predetermined measurement item and one of a plurality of predetermined measurement types;

wherein the controller is further programmed to perform instruction comprising steps of:

counting a first number of analysis for one of the plurality of the predetermined measurement types by the analyzing section during a first counting period, and counting a second number of analysis for one of the plurality of the predetermined measurement types by the analyzing section during a second counting period different from the first counting period;

wherein the step of counting comprises repeating counting the first number of analysis for one of the predetermined measurement types until counting for one of the predetermined measurement types with respect to each and every predetermined measurement item of plural predetermined measurement items is completed during the first counting period; and repeating counting the second number of analysis for one of the predetermined measurement types until counting for one of the predetermined measurement types with respect to each and every predetermined measurement item of plural predetermined measurement items is completed during the second counting period;

receiving a selection of one of the first counting period and the second counting period; and outputting to the outputting device the first number of analysis, or the second number of analysis associated with a selected counting period, the step of outputting further comprises:

switching a display of the first number of analysis to a display of the second number of analysis associated with the selected counting period;

displaying a table showing the first number of analysis, or the second number of analysis with respect to one of the predetermined measurement types and each and every predetermined measurement item; and displaying a filter button that prompts a filter dialogue that allows a user to designate an arbitrary counting period within one of the first counting period and the second counting period.

13. A sample analyzer comprising:

a measurement sample preparation section;

an analyzing section;

an outputting device;

a controller having a processor and a memory programmed to perform instructions comprising steps of:

receiving order information indicating a predetermined measurement item on which analysis is to be performed on a biological sample;

controlling the measurement sample preparation section to mix the biological sample and a reagent so as to prepare a measurement sample in accordance with the order information; and controlling the analyzing section to analyze the measurement sample, an analysis of the measurement sample being associated with the predetermined measurement item and one of a plurality of predetermined measurement types;

wherein the controller is further programmed to perform instruction comprising steps of:

receiving designation of an arbitrary counting period;

counting a number of analysis for the predetermined measurement item during a received designated counting period;

wherein the step of counting comprises repeating counting the number of analysis for the predetermined measurement item until counting for the predetermined measurement item with respect to each and every predetermined measurement type is completed during the received designated counting period;

outputting to the outputting device the number of analysis associated with the received designated counting period, the step of outputting further comprises:

displaying a table showing the number of analysis with respect to a predetermined measurement item and each and every predetermined measurement type during the received designated counting period; and displaying a filter button that prompts a filter dialogue that allows a user to designate the arbitrary counting period.

\* \* \* \* \*